United States Patent [19]

Zarnack et al.

[11] Patent Number: 5,777,119
[45] Date of Patent: Jul. 7, 1998

[54] PROCESS FOR THE PREPARATION OF 2,3-DIHALOGENOQUINOXALINES

[75] Inventors: Jens Uwe Zarnack, Brunsbüttel; Bernd Diesselkämper, Marne, both of Germany; Wolfgang Lorenz, New Martinsville, W. Va.; Jörg-Michael Borchers, Neufeld, Germany

[73] Assignee: Bayer Aktiengesellschaft, Leverkusen, Germany

[21] Appl. No.: 561,217

[22] Filed: Nov. 21, 1995

Related U.S. Application Data

[63] Continuation of Ser. No. 230,049, Apr. 19, 1994, abandoned.

[30] Foreign Application Priority Data

Apr. 26, 1993 [DE] Germany ............ 43 13 586.2

[51] Int. Cl.$^6$ ............................. C07D 241/44
[52] U.S. Cl. ............ 544/356; 544/353; 544/354
[58] Field of Search ............... 544/353, 354, 544/356

[56] References Cited

U.S. PATENT DOCUMENTS

| | | | |
|---|---|---|---|
| 4,309,182 | 1/1982 | Koll et al. ............... | 8/527 |

FOREIGN PATENT DOCUMENTS

| | | |
|---|---|---|
| 0023955 | 2/1981 | European Pat. Off. . |
| 0027964 | 5/1981 | European Pat. Off. . |
| 0050790 | 5/1982 | European Pat. Off. . |
| 0087703 | 9/1983 | European Pat. Off. . |
| 0281898 | 9/1988 | European Pat. Off. . |
| 0537540 | 4/1993 | European Pat. Off. . |
| 1186160 | 1/1965 | Germany . |
| 1469698 | 7/1969 | Germany . |
| 2948292 | 6/1981 | Germany . |
| 3039884 | 5/1982 | Germany ............... 544/356 |
| 3503745 | 8/1986 | Germany . |
| 315451 | 7/1929 | United Kingdom . |

OTHER PUBLICATIONS

Chemical Abstracts (General Chemistry), p. 4, Week E29; "Trichloromethyl quinoxaline cpds ... ", Bayer AG, Jun. 15, 1982, E13, 41665 E/21=J5 7095–968.

Chemical Abstracts (E: General Chemistry), vol. 90, No. 40, one page; E13:J9 0043736-B, J 9 0043737-B, and J9 0043745-B, Mitsui Toatsu Chem. Inc. (1990).

Chemical Abstracts (General Chemistry), p. 2; "Chlorination of alpha–hydroxy N–heterocyclic cpds ... ", Bayer AG, Jun. 18, 1982; 37577 E/19=J5 7098–274.

Chemical Abstracts (General Chemistry), p. 2, vol. 87, No. 23; "Chlorination of alpha–hydroxy N–heterocyclic cpds ... ", Bayer AG, Jun. 4, 1987, J8 7025663-B.

J. March, Advanced Organic Chemistry, Reactions, Mechanisms, and Structure, Mar. 3rd Edition, Chapter 10, pp. 286–287 and 316.

*Condensed Pyrazines* by G.W.H. Cheeseman and R.F. Cookson (1979) pp. 94–95, 168.

*Heterocyclic Compounds*, (Robert C. Elderfield, Editor) vol. 6, p. 480 (1957).

*Advanced Organic Chemistry* (2nd Ed.) by Jerry Murch (1977) pp. 341–342.

*Primary Examiner*—Emily Bernhardt
*Attorney, Agent, or Firm*—Sprung Kramer Schaefer & Briscoe

[57] ABSTRACT

Quinoxalines are prepared by reaction of oxalic acid with an o-phenylenediamine, halogenation in the presence of a solvent and oxidation to a quinoxaline carboxylic acid derivative.

6 Claims, No Drawings

PROCESS FOR THE PREPARATION OF 2,3-DIHALOGENOQUINOXALINES

This application is a continuation, of application Ser. No. 08/230,049, filed Apr. 19, 1994 now abandoned.

The invention relates to a new process for the preparation of quinoxalines, in particular 2, 3-dichloroquinoxaline-6-carboxylic acid chloride.

2,3-Dichloroquinoxaline-6-carboxylic acid chloride is an important intermediate product for the preparation of reactive dyestuffs. In such dyestuffs, the quinoxaline carboxylic acid chloride grouping functions as a reactive group which reacts chemically with the fibre.

Various preparation processes are already known for 2, 3-dichloroquinoxaline-6-carboxylic acid chloride. According to German Auslegeschrift 1,186,160, for example, a 1, 2-diaminobenzoic acid can be used as the starting substance and can be reacted with oxalic acid to form a quinoxaline ring, and the free hydroxyl groups can be converted into halogen substituents.

The disadvantage of the known processes is their comparatively unsatisfactory yield. The invention was based on the object of providing an improved preparation process.

The present invention relates to a process for the preparation of dihalogenoquinoxaline carboxylic acid halides of the formula

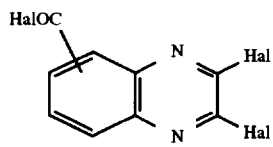

by condensation of the diamine II

with oxalic acid (III) to give compounds of the formula (IV)

```
COOH          (III)
|
COOH
```

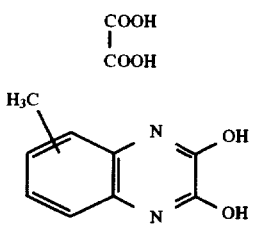

free radical or ionic halogenation, induced by heat or photochemically, preferably with chlorine in a solvent, to give (V)

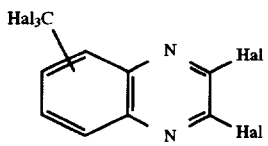

and oxidation to compounds of the formula (I), preferably by oxidation to the carboxylic acid (VI)

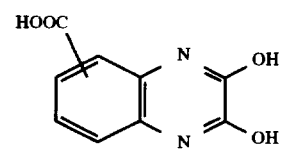

and halogenation to compounds of the formula (I).

In a preferred embodiment, the substituent $CH_3$ in formula (II) is not in the ortho-position relative to the two amino substituents. In a particularly preferred embodiment, the substituents $R^1$ and $R^2$ denote hydrogen. In an especially preferred embodiment, the end product 2, 3-dichloroquinoxaline-6-carboxylic acid chloride is obtained according to the invention starting from 3, 4-toluylenediamine as the compound II.

The halogenation is preferably carried out with light in the presence of a solvent. Suitable solvents are chlorinated aromatics, carbon tetrachloride, phosphorus oxychloride and, in particular, thionyl chloride. The halogenation can be carried out in the presence of a catalyst; suitable catalysts are pyridine and N,N-disubstituted formamides, in particular dibutylformamide. If the halogenation is induced thermally, commercially available free radical chain initiators, in particular azo-bis-isobutyronitrile, are additionally employed. The trihalogenoalkylquinoxaline derivative V can be converted into the dihydroxyquinoxalinecarboxylic acid VI by hydrolysis and replacement of the halogen substituents by hydroxyl groups. This reaction is carried out either with steam under elevated temperature or with the addition of alkali in aqueous solution at elevated temperature. The subsequent reaction comprises halogenation, in particular chlorination with phosgene, particularly preferably with thionyl chloride, to give compound I. This halogenation is, in general, carried out in the presence of a catalyst; suitable catalysts for the chlorination are pyridine and N,N-disubstituted formamides, in particular dibutylformamide.

Alternatively, the stage V can be converted to the end product I by oxidation with carboxylic acids and metal halides.

This oxidation is preferably carried out by reaction with formic acid in the presence of iron (III) chloride.

The new preparation process is based on only a few basic chemicals and gives, surprisingly, an overall yield of more than 95%.

The quinoxalines prepared according to the invention can be used for the preparation of reactive dyestuffs in the customary manner, in particular by reaction with dyestuffs containing amino groups or dyestuff precursors. Reference is made to German Auslegeschrift 1,469,698, DE-A 2,948, 292, DE-A 2,948,293, DE-A 2,925,210, DE-A 2,942,964, DE-A 3,207,534, DE-A 3,503,745 and DE-A 3,707,549.

EXAMPLE

1st Reaction stage 180 g of oxalic acid are dissolved in 1,500 ml of water and the solution is heated to 98° to 100° C. When the stated temperature has been reached, 122 g of 3, 4-diaminotoluene are carefully added dropwise to the oxalic acid solution. The precipitated 6-methyl-2, 3-quinoxalinedione/-diol is filtered off with suction over a suction filter and washed free from amine with hot water. Drying is carried out at 120° C. in a heating cabinet.

Yield: 173.4 g (0.99 mol)=98.5% of theory.

2nd Reaction stage:

641 g of thionyl chloride and 2 g of N,N-dibutylformamide are added to 173.4 g of 6-methyl-2,3- quinoxalinedione/-diol from the 1st reaction stage. The mixture is carefully heated to the boiling point. When the boiling point has been reached, Cl₂ gas is passed into the reaction mixture, while irradiating with UV. The rate of introduction should be about 40 l/hour. The course of the reaction is monitored by thin layer chromatography. After about 5 hours, the reaction has ended. The unused thionyl chloride can be distilled off under 15 mbar under a water pump vacuum at 40° C. The 2,3-dichloro-6-trichloromethylquinoxaline formed remains.

Yield: 307.8 g (0.97 mol)=98.7% of theory.

3rd Reaction stage:

307.8 g of 2,3-dichloro-6-trichloromethylquinoxaline are taken up in 2,000 ml of boiling water. Superheated steam is then blown in. To trap the hydrochloric acid thereby formed, 220 g of sodium hydroxide are added. For working up the preparation, the batch is first filtered. The filtrate is then acidified with hydrochloric acid and the pure quinoxaline-6-carboxylic acid precipitates out. This is filtered off with suction over a suction filter and washed free from acid with hot water. For drying, the substance is placed in a heating cabinet at 120° C.

Yield: 196.5 g (0.95 mol)=99.4% of theory.

4th Reaction stage 196.5 g of quinoxaline-6-carboxylic acid are heated under reflux with the addition of 600 g of thionyl chloride and 2 g of N,N-dibutylformamide. During this procedure, HCl is formed and the carboxyl and hydroxyl groups are thereby chlorinated. The excess thionyl chloride is then distilled off under a water pump vacuum. The end product is freed from residues of thionyl chloride still present in a desiccator under a vacuum of 0.5 mbar.

Yield: 243.4 g (0.95 mol)=98.9% of theory.

We claim:

1. Process for the preparation of dihalogenoquinoxalines of the formula (I)

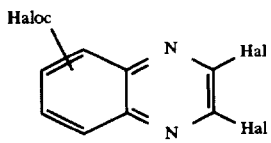
(I)

by condensation of the diamine II

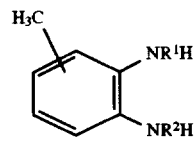
(II)

with oxalic acid (III)

$$\begin{array}{c}\text{COOH}\\|\\\text{COOH}\end{array}$$
(III)

to form compounds of the formula (IV),

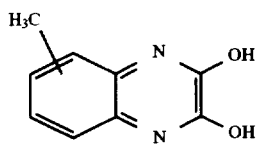
(IV)

followed by halogenation of (IV) with chlorine and thionyl chloride, in a one-step reaction wherein thionyl chloride is used as both a solvent and a halogenating agent, to form compounds of the formula (V)

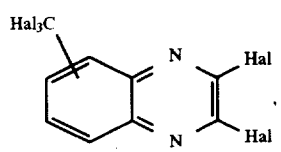
(V)

and oxidation of the compounds of formula (V) to form the compounds of formula (I), wherein R¹ and R² independently of one another denote hydrogen or C₁-C₄ alkyl, followed by, Hal denotes Cl.

2. Process according to claim 1, characterized in that the substituent CH₃ in compound II is not in the ortho-position relative to the amino groups in the formula II.

3. Process according to claim 1, wherein R¹ and R² denote hydrogen.

4. Process according to claim 1, wherein the halogenation is carried out in the presence of a halogenation catalyst selected from the group consisting of pyridine, N,N-disubstituted formamide and azo-bis-isobutyronitrile.

5. Process according to claim 1, wherein the oxidation of the intermediate product V to I is carried out by converting compound (V) to

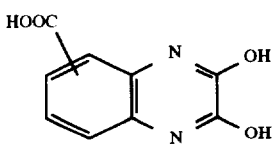
(VI)

by hydrolysis and replacement of the halogen substituents by hydroxyl groups, either with steam at elevated temperatures or with the addition of alkali in an aqueous solution at elevated temperatures, and halogenation of compound (VI) to compound (I).

6. Process according to claim 1, wherein the oxidation of the intermediate stage V to I is carried out by reaction with formic acid in the presence of a metal halide catalyst.

* * * * *